United States Patent [19]

Nogrady

[11] 4,232,002
[45] Nov. 4, 1980

[54] PROCEDURES AND PHARMACEUTICAL PRODUCTS FOR USE IN THE ADMINISTRATION OF ANTIHISTAMINES

[75] Inventor: Stephen G. Nogrady, Sully, near Penarth, Great Britain

[73] Assignee: The Welsh National School of Medicine, Penarth, Great Britain

[21] Appl. No.: 965,171

[22] Filed: Nov. 30, 1978

[30] Foreign Application Priority Data

Dec. 1, 1977 [GB] United Kingdom ............... 50020

[51] Int. Cl.$^2$ .................. A61L 9/04; A61K 9/04; A61K 31/44
[52] U.S. Cl. ........................... 424/45; 424/46; 424/263
[58] Field of Search ............... 424/263, 46, 45

[56] References Cited

PUBLICATIONS

American Hospital Formulary Service, 1966, 4:00 Antihistamine Drugs.

Primary Examiner—Stanley J. Friedman
Attorney, Agent, or Firm—Young & Thompson

[57] ABSTRACT

An antihistamine of the benzhydrylether, alkylamine, or benzocyloheptatiophene class is suitable for use in the therapeutic treatment or prophylaxis of reversible airways obstruction by inhalation. The antihistamine may be clemastine, chlorpheniramine or ketotifen and may be in the form of a composition in admixture with a diluent. The antihistamine can be administered from a pharmaceutical inhalation device which is designed to administer a dosage unit of the antihistamine. The inhalation device can be in the form of a pressurized aerosol inhaler or a dry powder insufflator.

5 Claims, No Drawings

PROCEDURES AND PHARMACEUTICAL PRODUCTS FOR USE IN THE ADMINISTRATION OF ANTIHISTAMINES

The present invention relates to methods, and pharmaceutical preparations or charges intended for use in the treatment, by inhalation, of reversible airways obstruction, as for example, in asthma, chronic bronchitis, and allergic conditions commonly known as hay fever. The invention is particularly valuable in cases where rapid relief is desired.

The role of histamine in the mediation of bronchial asthma is controversial. Histamine has been shown to be released, along with other mediators, from the lungs of guinea pigs previously sensitized by allergen exposure, upon re-challenge with the same allergen. The injection of histamine in some animals provokes an anaphylactoid reaction which includes severe broncho-spasm. In man, the injection of histamine, or its inhalation has various effects. In normal subjects quite large doses can be tolerated with only mild visceral effects (rapid pulse, abdominal discomfort, headache, and flushing). However, in patients with asthma, chronic bronchitis, and hay fever, even very small doses of histamine, either by injection or aerosol inhalation, excite intense bronchoconstriction. Finally, it has been shown that blood histamine levels are higher in asthmatics than in non-astmatic subjects, and rise significantly following allergen induced bronchoconstriction, and in spontaneously occurring attacks. Sputum histamine levels are also elevated in patients with chronic bronchitis in exacerbation.

These studies suggested that antihistamines might have a place in the blocking and treatment of exacerbations of these conditions. However, numerous studies have failed to show any significant benefit from antihistamine given orally, or by injection, in doses tolerable in the patient.

It has now been found that useful effects may be obtained by direct inhalation of specific classes of antihistamines.

Broadly stated, from one aspect the invention consists in a pharmaceutical composition for use in the therapeutic treatment or prophylaxis of reversible airways obstruction by inhalation, containing as an active ingredient an antihistamine of the benzhydrylether, alkylamine or benzocycloheptathiphene class in admixture with a diluent.

The composition may be in the form of a nebuliser solution, liquid suspension or dry powder.

The preferred antihistamines are clemastine and chlorpheniramine, preferably in the form of fatty acid salts, the chlorpheniramine salts being derived from fatty acids having from 1 to 6 carbon atoms.

There is also provided, according to the invention, a method for the treatment or prophylaxis of reversible airways obstruction, by inhalation of an antihistamine of the benzhydrylether or alkylamine class.

Preferably clemastine, which belongs to the Benzhydrylether class, is in the form of the hydrogen fumerate of 1 (Methyl. 2 2-Methyl-p-chlordiphenyl methyloxy)ethyl pyrolidin. Chlorpheniramine, preferably as the maleate salt, is in the alkylamine class which also includes Brompheniramine Maleate.

The dosage, i.e. the effective quantity of the antihistamine drug inhaled at each inhalation, can be critical and according to a preferred feature of the invention each inhalation provides the equivalent of 0.1 to 5 mg. of clemastine, or 0.05 to 2.5 mg. of chlorpheniramine. The drug may be inhaled in the form of a mist or nebulized spray, or as a cloud of fine solid particles, and may be inhaled from a variety of inhaler devices. For example, the inhaler device may be in the form of a pressurised canister inhaler containing a propellant gas together with the active drug, and having an automatic volumetric dosage meter to determine the volume and hence the quantity of drug administered on each actuation of the inhaler. Alternatively, the inhaler device may be in the form of a portable dry powder insufflator containing a prepared capsule containing a measured quantity of the drug. The drug may also be inhaled as an aerosol generated in a nebulizer device driven by compressed air or oxygen.

The inhaler device may be designed to administer a predetermined dosage unit of the drug, i.e. 0.1 to 5 mg of clemastine, or 0.05 to 2.5 mg of chlorpheniramine.

In a further form, the device consists of an insufflator, comprising a tube having a mouthpiece, an air inlet, a turbo-mixer (a device for inserting the powder into the air stream), and a means of receiving and cutting or piercing a capsule containing a dry powder including the antihistamine drug.

The device may also be in the form of a pressurised aerosol inhaler, comprising a canister containing a propellant gas combined with a solution or suspension of the drug and a dispensing-metering valve for dispensing predetermined volumes of the contents, the metered volume and the strength of the solution or suspension in the container being such as to provide the required dosage.

For convenience of use, the drug may be packaged in the form of a capsule containing a dry powder dose for use in an insufflator, the capsule containing a mixture of the antihistamine and an inert dry powder micronised filler.

For use in a nebulizer device, either as a pressurised aerosol inhaler or as an oxygen or compressed air driven device, the drug would normally be provided as a solution or suspension having suitable viscosity, surface tension, and other properties for direct local application to the bronchi. A suitable viscosity is between 5 and 40 centipoise. The ingredients of the solution or suspension may include some, or all, of the following:

(a) The active agent.
(b) Water, saline or ethanol (to make the solution).
(c) Stabiliser such as Propylene glycol. (See below)
(d) Preservatives.
(e) Surface active agents ('wetting agents') to aid droplet formation and stability.
(f) Emulsifying agents, e.g. soya bean, lecethin or oleic acid.
(g) Antioxidants.
(h) Flavourings.
(i) Buffer Solution.

An example of a nebulizer solution or suspension is as follows:

| | |
|---|---|
| Clemastine | 0.001 g |
| Fumaric acid | 0.0034 g |
| Sorbitol | 0.045 g |
| Ethanol (94% w/w) | 0.07 g |
| Propylene glycol | 0.3 g |
| Tribasic sodium citrate dihydrate | to pH 6.3 |

| | |
|---|---|
| Water | to 1.027 g = 1 ml. |

The above corresponds to a 0.1% solution which is diluted with normal saline to produce a 0.05% solution. This is then placed in a nebulizer.

An alternative method of inhalation is by means of a pressurised canister or so-called aerosol dispenser. Such canisters are commercially available fitted with automatic metering dispensing valves designed to discharge a predetermined volume of the contents on each pressure actuation. Examples are given in British Pat. Nos. 830,427 and 994,755 of Riker Laboratories Inc.

Pressurised canisters of this type are charged with a mixture of the active ingredient with a propellant agent, usually a mixture of propellant gases. Such gases are well-known and the principal halogenated hydrocarbon gases have been provided with an international indexing system. The principal gases used for medical applications are:

C11—trichlorofluoromethane
C12—dichlorofluoromethane
C114—dichlorotetrafluoroethane The liquid contents of the canister may also include some or all of the further ingredients mentioned above for a nebulizer solution.

An example of a composition useful in a pressurised "aerosol" canister is:

| | |
|---|---|
| Clemastine hydrogen fumarate | .134 mg |
| Soyabean lecithin | 0.1 mg |
| Ethanol absolute | 5.0 mg |
| Frigen 113TR (trichlorotri-fluoroethane) | 20.0 mg |
| Frigen 11/12/114 (25:50:25 by volume) | 61.0 mg |

The above corresponds to a single dose. An amount of composition corresponding to 100 such doses is prepared and filled into a pressurised aerosol container.

In these liquid preparations Propylene glycol has four potential effects:

(a) It improves the solubility of the compound in its vehicle e.g. water, saline, or ethanol.

(b) It may improve the stability of the compound in solution.

(c) It has 'surface active properties' and enables mixing of the agent solution with the propellant enabling the released metered dose from the canister to contain the right proportion of agent solution and propellant.

(d) It increases the stability of the aerosol droplets after release into the air to prevent clumping and dispersion.

When administered in the form of a dry powder with an insufflator the drug is usually provided together with an inert harmless powder filler, e.g. lactose in a micronised condition, ground to a particle size in the micron range. The powder mixture is usually packed into a small capsule or container which is partly filled.

The dosages provided may be critical both from a medical and a practical point of view. In the case of a nebulizer solution the actual quantity of a dose will normally be about 1 or 2 ml, sufficient for an average nebulizer container. Volumes of less than 0.5 ml are difficult to nebulize due to losses and volumes greater than 5 ml take too long to be nebulized. The strength of the clemastine solution will therefore usually be 0.1 to 5.0 mgm/ml with an ideal solution around 1 mg/ml. For chlorpheniramine the solution strength will be 0.05 to 2.5 mgm/ml with an ideal solution around 0.5 mg/ml.

For a pressurised "aerosol" canister inhaler the strength of the solution or suspension should be related to the automatic metering dispenser to provide the required dose for inhalation. For clemastine the dose is preferably in the range 0.1 to 0.5 mg, and with chlorpheniramine 0.05 to 2.5 mg. It is anticipated that normally one to two actuations will be recommended for each inhalation and on this basis the strength of the solution can be calculated. Up to four actuations may, however, be acceptable.

For dry powder inhalation the preferred clemastine dose is 0.1 to 6 mg. and for chlorpheniramine 0.05 to 2.5 mg. In each case the dose is made up with dry powdered lactose or similar filler to a suitable volume for insufflation from the capsule. In use the capsule is fitted in a portable insufflator provided with a device for puncturing the capsule and a small turbo-mixer which creates a dispersed cloud when the patient inhales through the mouthpiece.

The following examples illustrate the invention in more detail:

EXAMPLE 1

Pilot Study in Asthmatics

Five patients were studied when recovering from a severe attack of asthma. Patients 1, 2 and 3 inhaled chlorpheniramine 0.05% and patients 4 and 5 inhaled clemastine 0.05% from a Wright's nebulizer. Baseline measurements of blood pressure and $FEV_1$ and FVC (Forced Vital Capacity) were taken and repeated at 10 minute intervals for 1 hour following inhalations of the test substances (see Table 1). No change in blood pressure was noted and the inhalation was well tolerated by all the patients.

These studies suggested a useful degree of bronchodilatation and prompted a formal study.

TABLE 1

| Pilot study of inhaled chlorpheniramine and clemastine in asthma. | | |
|---|---|---|
| Patient | Inhalation | Maximum % Change in $FEV_1$ |
| CE | Chlorpheniramine 0.05% | 25% |
| ES | Chlorpheniramine 0.05% | 38% |
| GA | Chlorpheniramine 0.05% | 25% |
| BS | Clemastine 0.05% | 100% |
| JP | Clemastine 0.05% | 23% |

EXAMPLE 2

Formal Study of Clemastine in Bronchial Asthma

This was a double blind study comparing the bronchodilating properties of clemastine with an established bronchdilator drug (Salbutamol), and a placebo (Saline) given by inhalation.

12 patients (age range 29–70 years—mean 46 years) gave informed consent. All were recovering from a severe exacerbation of bronchial asthma and were in a stable clinical state. All had previously demonstrated reversibility of airways obstruction by a greater than 15% increase in Peak Expiratory Flow Rate (PEFR) following inhalation of Salbutamol aerosol 200 μgms. 6 of the 12 patients were atopic, in that they demonstrated an immediate skin reaction to more than one allergen on prick testing.

On 3 consecutive mornings the patients had baseline measurements of PEFR using a Wright's Peak Flow Meter and FEV1 using a dry-wedge spirometer (Vitalograph), Each subject inhaled from a Wright's nebulizer 1 ml each of clemastine 0.05% Salbutamol 0.05% and normal saline placebo administered on consecutive days in a sequence determined randomly. PEFR and FEV1 were measured at 5, 15, 30, 45, 60, 90, 120, 180 and 240 minutes after the inhalation. Results were analysed using Students' 't' test for paired samples.

Results

Mean baseline PEFR was 283±100 liters per minute. Following Salbutamol inhalation there was a mean increase of 35.2% at 45 minutes. Following clemastine inhalation, mean PEFR rose by 31.2% at 60 minutes. There were no significant differences between the changes obtained with clemastine and Salbutamol. There was a 15% placebo response, but both active drugs performed significantly better than placebo. At 240 minutes the response to clemastine was still 20.2% while for Salbutamol it had fallen to 12.0%. This mean baseline FEV1 was 2.00±0.78 liters. Following Salbutamol inhalation this rose by 29.2% at 90 minutes. With clemastine there was a 21.1% increase in FEV1 at 60 and 90 minutes. At 240 minutes the response to Salbutamol has fallen by 4.3% but was maintained at 10.4% with clemastine.

TABLE 2

Percentage Change in PEFR with Salbutamol, Clemastine & Placebo (± S.D.)

| Time | Salbutamol | Clemastine | Placebo |
|------|------------|------------|---------|
| 5 | 23.3 ± 27.7 | 16.2 ± 25.5 | 10.0 ± 20.9 |
| 15 | 29.3 ± 34.0 | 23.6 ± 27.2 | 9.3 ± 20.4 |
| 30 | 31.4 ± 32.8 | 23.5 ± 30.0 | 10.6 ± 21.3 |
| 45 | 35.2 ± 37.3 | 27.5 ± 33.2 | 13.8 ± 15.4 |
| 60 | 34.1 ± 35.3 | 31.2 ± 31.6 | 13.7 ± 18.0 |
| 90 | 34.5 ± 34.5 | 29.2 ± 33.0 | 13.3 ± 19.6 |
| 120 | 31.8 ± 32.9 | 27.6 ± 27.4 | 15.0 ± 15.4 |
| 180 | 23.9 ± 26.8 | 23.5 ± 15.4 | 14.2 ± 19.3 |
| 240 | 4.31 ± 14.8 | 10.4 ± 16.4 | 0.13 ± 11.4 |

TABLE 3

Percentage change in FEV1 with Salbutamol, Clemastine & Placebo (± S.D.)

| Time | Salbutamol | Clemastine | Placebo |
|------|------------|------------|---------|
| 5 | 19.7 ± 25.0 | 9.1 ± 17.3 | 4.8 ± 21.2 |
| 15 | 21.2 ± 23.1 | 13.3 ± 22.4 | 6.6 ± 21.8 |
| 30 | 27.3 ± 23.3 | 18.1 ± 18.7 | 8.4 ± 20.7 |
| 45 | 23.2 ± 24.8 | 20.4 ± 21.5 | 7.3 ± 16.5 |
| 60 | 26.4 ± 26.5 | 21.1 ± 22.3 | 7.7 ± 22.5 |
| 90 | 29.2 ± 26.1 | 21.1 ± 20.6 | 9.1 ± 20.3 |
| 120 | 20.6 ± 18.2 | 17.8 ± 20.2 | 13.1 ± 16.2 |
| 180 | 11.8 ± 19.3 | 15.2 ± 17.8 | 9.8 ± 21.1 |
| 240 | 4.31 ± 14.8 | 10.4 ± 16.4 | 0.13 ± 11.4 |

Conclusion

This study suggested that clemastine aerosol is an effective bronchodilator, comparable with Salbutamol and having a prolonged action.

EXAMPLE 3

Studies of Small Airways Function with Inhaled Clemastine

10 Asthmatic patients gave informed consent to the study. All were known to have reversibility of airways obstruction in that they had previously demonstrated a greater than 15% increase in PEFR with inhalation of Salbutamol 200 μgms. All were patients and were in a stable clinical state. The study was divided into two sessions, generally the morning and afternoon of the same day.

At each session, baseline measurements of FEV1, FVC and PEFR were obtained, as well as measurement of maximum expiratory flow at 50% and 25% of forced vital capacity. The latter test was performed using an Ohio spirometer giving flow and volume signals which were plotted separately against time and then integrated to give measurements of flow at the given divisions (50% and 25%) of forced vital capacity.

Following this the patient inhaled clemastine 0.05% at one session and saline placebo at the other. These were administered single blind in a random sequence.

The measurements mentioned were repeated at 5, 15, 30, 60, 90 and 180 minutes following inhalation. (see Table 4).

TABLE 4

|  | Mean maximum % increase (clemastine) | Mean maximum % increase (saline) |
|---|---|---|
| FEV1 | 11.47 | 2.52 |
| FVC | 8.10 | 3.67 |
| PEFR | 18.5 | 7.75 |
| $MEF_{50}$ | 43.6 | 5.85 |
| $MEF_{25}$ | 89.68 | −3.24 |

Conclusion

In stable asthmatic patients in recovery there was a small increase in tests of obstruction of large airways. In chronic stable asymptomatic asthmatic patients there is a large degree of small airways obstruction which is not detectable by tests such as FEV1, FVC and PEFR, but can be indirectly assessed by maximum expiratory flow rates at low lung volumes ($MEF_{50}$ and $MEF_{25}$). It is clinically important in causing diminished respiratory reserve in these patients. The highly significant increase in flow rates with these tests suggests opening up of peripheral small airways.

EXAMPLE 4

Studies into Mode of Action

Methods 10 consenting asthmatic patients in remission had baseline measurements of airways obstruction by means of FEV1, FVC and PEFR measured by a McDermott spirometer (M.R.C. design) as well as measurements of lung volume, airways resistance and specific airways conductance measured by whole bodied plethysmography. Following this, patients inhaled, on two separate days, 1 ml of either normal saline placebo or clemastine 0.1% solution delivered by a Hudson nebulizer driven by compressed air. Measurements were repeated at 30 minutes, and following this the patient underwent bronchial challenge with histamine. Five breaths of increasing concentration of histamine, were inhaled at 3 minute intervals from a similar Hudson nebulizer. Measurements of airways resistance were made at each dose intervals and the experiment terminated when the airways resistance increased by 100% or specific airways conductance fell to 50% of baseline values. The concentration of histamine responsible for these changes was taken as the threshold concentration.

Results

TABLE 5

| | |
|---|---|
| Mean threshhold concentration with saline: | 3.3 ± 3.8 mg/ml |
| Mean threshhold concentration with clemastine: | 44.1 ± 37.0 mg/ml |

This means that, when pretreated by inhalation of clemastine, patients were able to tolerate a 13 fold increase in histamine induced bronchoconstriction. This confirms a highly significant blocking action.

EXAMPLE 5

Studies with Portable Pressurised Canister Inhalers 7 stable consenting asthmatic subjects recovering from a severe exacerbation of bronchial asthma, but who were in a stable clinical state were studied. All had previously demonstrated a reversibility of airways obstruction by a greater than 15% peak expiratory flow rate following inhalation of salbutomol aerosol.

On three consecutive mornings the patients had baseline measurements of $FEV_1$ using a dry wedge spirometer (Vitalograph). Each subject then inhaled two puffs of either placebo, clemastine 0.01 mg/puff, or clemastine 0.1 mg/puff. One of each of the inhalations was given on the three days of the study in a random sequence and double blind. The agents were administered from a portable pressurised canister aerosol device. $FEV_1$ was measuired at 5, 15, 30, 60, 90, 120, 180, 240 and 360 minutes after inhalation. There was no significant difference between mean baseline values of $FEV_1$ on the three treatment days. With placebo the maximum percentage increase in $FEV_1$ was 4.9% achieved at 180 minutes. With clemastine 0.01 mg/puff 2 puffs provided a maximum mean percentage increase in $FEV_1$ of 9.8±11.75% at 3 hours. With inhalation of clemastine 0.1 mg/puff, two inhalations resulted in a mean maximum percentage increase in $FEV_1$ of 18.71%. The percentage increase in $FEV_1$ with this dose was highly significant and superior to the placebo response.

No side effects were complained of by the patients studied, and in particular the taste of the preparation was found to be quite tolerable.

Although the specific examples have described the use of clemastine and chlorpheniramine, the invention also encompasses the antihistamine ketotifen (of the benzocycloheptathiophene group). Ketotifen is preferably used in the form of the acid fumarate, although it can be used in the form of any fatty acid salt.

I claim:

1. A method for the treatment or prophylaxis of reversible airways obstruction in human patients, comprising administering by inhalation to a said patient a therapeutically or prophylactically effective amount of a member selected from the group consisting of clemastine, chlorpheniramine, ketotifen, brompheniramine, and a pharmaceutically acceptable salt thereof, said amount being effective for the treatment or prophylaxis of reversible airways obstruction.

2. A method as claimed in claim 1, in which said member is present in a composition comprising a liquid diluent, a dry powder or a liquefied propellant gas.

3. A method as claimed in claim 1, in which said effective amount is such that each inhalation provides the equivalent of 0.1 to 5 mg. of Clemastine, or 0.05 to 2.5 mg. of chlorpheniramine.

4. A method as claimed in claim 1, in which said member is inhaled in the form of a mist or nebulized spray, or as a cloud of fine solid particles.

5. A method as claimed in claim 1, in which said member is inhaled as an aerosol generated in a nebulizer device driven by compressed air or oxygen.

* * * * *